United States Patent
Blake, III

Patent Number: 6,077,233
Date of Patent: Jun. 20, 2000

[54] BLOOD COAGULATION TEST SYSTEM

[76] Inventor: Joseph W Blake, III, 77 Locust St., New Canaan, Conn. 06840

[21] Appl. No.: 09/041,522

[22] Filed: Mar. 12, 1998

[51] Int. Cl.[7] ..................................................... A61B 5/00
[52] U.S. Cl. ........................... 600/573; 73/64.41; 422/73; 422/69; 600/584; 600/580
[58] Field of Search .................................... 600/573, 575, 600/578, 580, 584; 73/54.01, 54.06, 54.11, 64.41; 422/68.1, 73; 436/69, 70

[56] References Cited

U.S. PATENT DOCUMENTS

| | | | |
|---|---|---|---|
| 3,912,455 | 10/1975 | Lichtenstein | 600/575 |
| 4,181,121 | 1/1980 | Schwoboda et al. | 600/575 |
| 4,296,748 | 10/1981 | Kurtz et al. | 600/575 |
| 4,551,308 | 11/1985 | Mintz | 422/73 |
| 4,604,894 | 8/1986 | Kratzer et al. | 422/73 |
| 5,047,211 | 9/1991 | Sloane, Jr. et al. | 422/73 |
| 5,051,239 | 9/1991 | Von Der Goltz | 422/73 |
| 5,078,704 | 1/1992 | Wejnar | 600/573 |
| 5,302,348 | 4/1994 | Cusack et al. | 422/73 |
| 5,339,830 | 8/1994 | Blake, III | 73/64.41 |
| 5,735,834 | 4/1998 | Hemstreet et al. | 600/584 |

Primary Examiner—Cary O'Connor
Assistant Examiner—Charles Marmor, II
Attorney, Agent, or Firm—Patrick J. Walsh

[57] ABSTRACT

A blood coagulation test system for in vitro assessment of blood characteristics including hemostasis, thrombus formation, thrombolysis, and collagen platelet interaction comprises a test unit for collection, testing and disposal of the sample together with a test analyzer for executing a test protocol. Coagulation functions are evaluated by establishing controlled bleeding of the sample from a bleeding tube within the unit and monitoring these blood characteristics as a function of blood pressure variations occurring in the unit as the test proceeds. The blood sample remains within the unit for testing and after disposal.

17 Claims, 5 Drawing Sheets

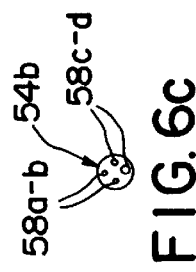
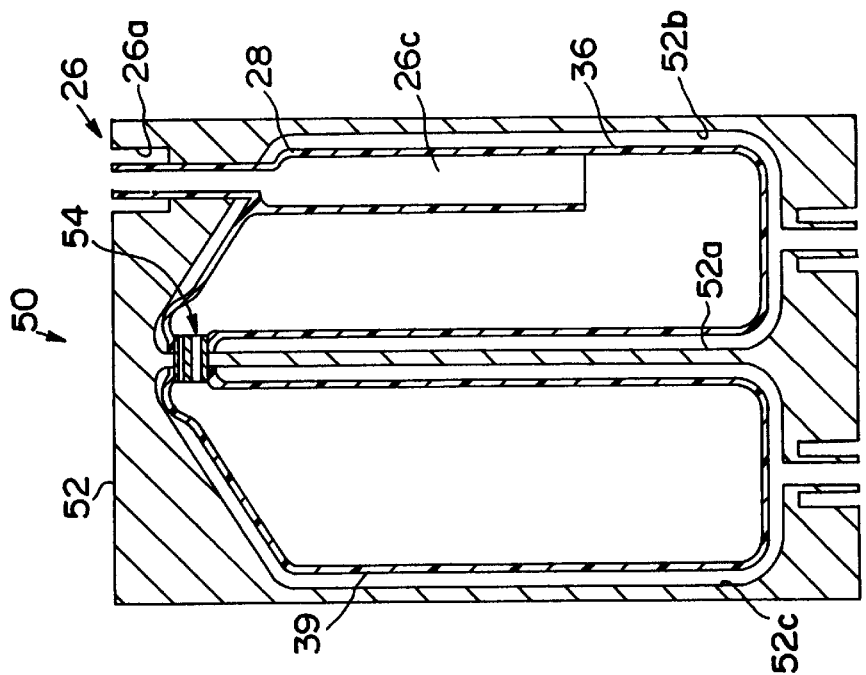
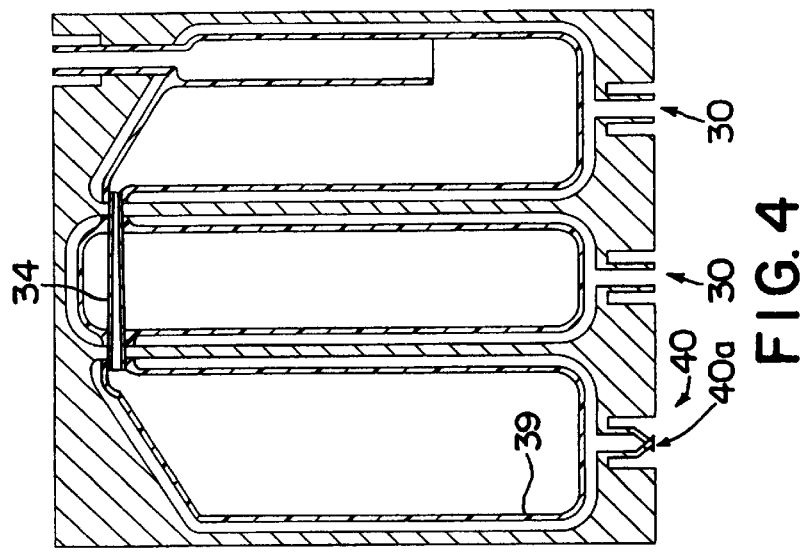

BLOOD COAGULATION TEST SYSTEM

BACKGROUND OF THE INVENTION

The present invention relates to blood coagulation tests and particularly to such tests performed in vitro.

It is desirable to assess and monitor blood characteristics including hemostasis (cessation of venous or arterial bleeding), clotting or thrombus formation, and thrombolysis (dissolving or shrinking clots in the blood stream) for a variety of medical procedures as for example treating blood disorders such as hemophilia, performing surgery, and blood transfusions. Such blood assessments are required promptly for surgical procedures, emergency room treatments, or blood transfusions and must be performed without the benefit of laboratory test conditions. In addition, aging and handling of a blood sample have significant effect on the blood clotting mechanism. Therefore it is necessary to provide a simple, on-site technique for in vitro assessment of blood characteristics as soon as practicable after a blood sample is drawn. The technique must also provide reliable, reproducible results.

My U.S. Pat. No. 5,339,830 is directed to a system for assessment of blood coagulation characteristics. The system includes a cartridge for collecting, assessing, and disposing of a blood sample. Hemostasis, clot formation, thrombolysis, and platelet collagen interaction properties of a set of blood samples drawn from a patient may be evaluated. The system further includes a test analyser for receiving the cartridge and for performing tests on individual sample cartridges.

As disclosed in said patent, in vitro blood analysis is performed reliably and repeatably immediately after sample collection under test conditions of constant temperature, pressure, and flow rate with minimal manipulation, agitation, and mechanical stress of the sample and without the use and disposal of supplies and related apparatus for stirring agents such as paraffin and saline solution. Bleeding aperture geometry is precisely controlled for achieving test repeatability and reliability. Disposal is limited to a test cartridge entirely containing the waste blood sample.

SUMMARY OF THE INVENTION

The present invention is directed to improvements to in-vitro blood analysis with particular emphasis on reliability and repeatability of results under test conditions of constant temperature, pressure, and flow rate with minimal manipulation, agitation, and mechanical stress of the sample.

In accordance with the invention, a test unit comprises a housing divided into a plurality of chambers lined with film bladders for receiving and testing a blood sample.

In a preferred embodiment of the invention, a test unit comprises a rigid housing divided into three side-by-side chambers by a pair of upstanding interior partition walls. Each of the side-by-side chambers has a film bladder therein. Blood samples are always confined to the interior of one or more of the film bladders, and for clear expression in this regard, the chamber defined by the bladder interior is referred to as bladder chamber while the chambers defined by the housing and its partitions are referred to as housing chambers.

Air overpressure, underpressure, and ambient pressure are selectively applied to the housing chambers to manipulate the bladder chambers for the purpose of drawing blood into a bladder chamber, (i.e, underpressure), for expelling a blood sample from a chamber (i.e., overpressure), and for controlling blood flow into a chamber (i.e., differential overpressure). The intermediate bladder chamber receives a bleeding sample with its housing chamber at ambient pressure.

The first of the bladder chambers includes a one-way valve for admitting a blood sample to the chamber. The housing chamber is evacuated to aid the bladder chamber in drawing in a blood sample through the one-way valve.

A bleeding tube interconnects all three bladder chambers preferably along the top portions of the chambers. The bleeding tube has an access opening for receiving a flow of blood at the top of the first bladder chamber. The tube is fitted with a bleeding hole intermediate its length for bleeding the blood sample into the second or intermediate bladder chamber. Finally, the tube has an exit opening for flow of the blood sample into the third or last of the chambers.

In preferred form, the first and third chambers have inlet and outlet ports at the highest point of the bladders for directing blood flow with minimal air entrainment into and away from the access and exit openings of the bleeding tube.

In operational phase, the first housing chamber is evacuated and a blood sample is drawn from patient into the first bladder through a one-way valve. Next, overpressure is applied to the first chamber housing to initiate blood sample flow into the bleeding tube through its access opening.

The intermediate bladder receives a portion of blood flow through a bleeding hole in the bleeding tube. The pressure in the intermediate chamber on the intermediate bladder chamber is maintained at ambient.

The remainder of the blood sample flows past the bleeding hole along the bleeding tube and through the exit opening into the third bladder chamber. The third housing chamber is either set at a positive pressure less than the pressure set for the first housing chamber, or being set at the same pressure thereafter develops a lower pressure than the first chamber by reason of bleed off of the blood sample into the intermediate chamber maintained at ambient. The pressure differential effects blood flow through the bleeding tube by maintaining a back pressure precisely regulating flow through the tube.

In this way hemostasis of a blood sample is determined at the point at which bleeding stops through the bleeding hole. Thrombus of the sample is determined at the point at which a clot forms in the bleeding tube stopping all blood flow.

A stabilized flow of blood through the system will gradually create a back pressure, over a period of time, within the chamber with occlusion of the bleeding tube. The increase of pressure over the stabilized system flow pressure is translated by an appropriate sensor into data when combined with elapsed time.

OBJECTS OF THE INVENTION

It is an object of the invention to provide a system for in vitro assessment of blood properties including hemostasis, clotting or thrombus formation.

Another object of the invention is to provide a test system for drawing a blood sample at an even flow rate to minimize the possibility of platelet activation.

It is an object of the invention to provide a totally contained unit for blood assessment which entirely contains a blood sample from collection through evaluation.

It is a further object of the invention to provide a test analyser in cooperation with a test unit in which blood assessment is performed under conditions of constant temperature, pressure and flow rate.

It is a further object of the invention to provide a system for evaluating blood properties immediately after collection of a blood sample.

It is a further object of the invention to provide for direct infusion of a blood sample from patient to the test unit.

Other and further objects of the invention will occur to one skilled in the art with an understanding of the following detailed description of the invention or upon employment of the invention in practice.

DESCRIPTION OF THE DRAWING

A preferred embodiment of the invention has been chosen for purposes of illustrating the construction and operation of the invention and is shown in the accompanying drawing in which:

FIG. 4 is a full vertical section view of another embodiment of the housing and bladder chambers according to the invention.

FIGS. 6a–c are a full vertical section view of a modified embodiment of the invention having two housing and bladder chambers, and bleeding passageways between the housings.

DETAILED DESCRIPTION OF THE INVENTION

Figure 1:
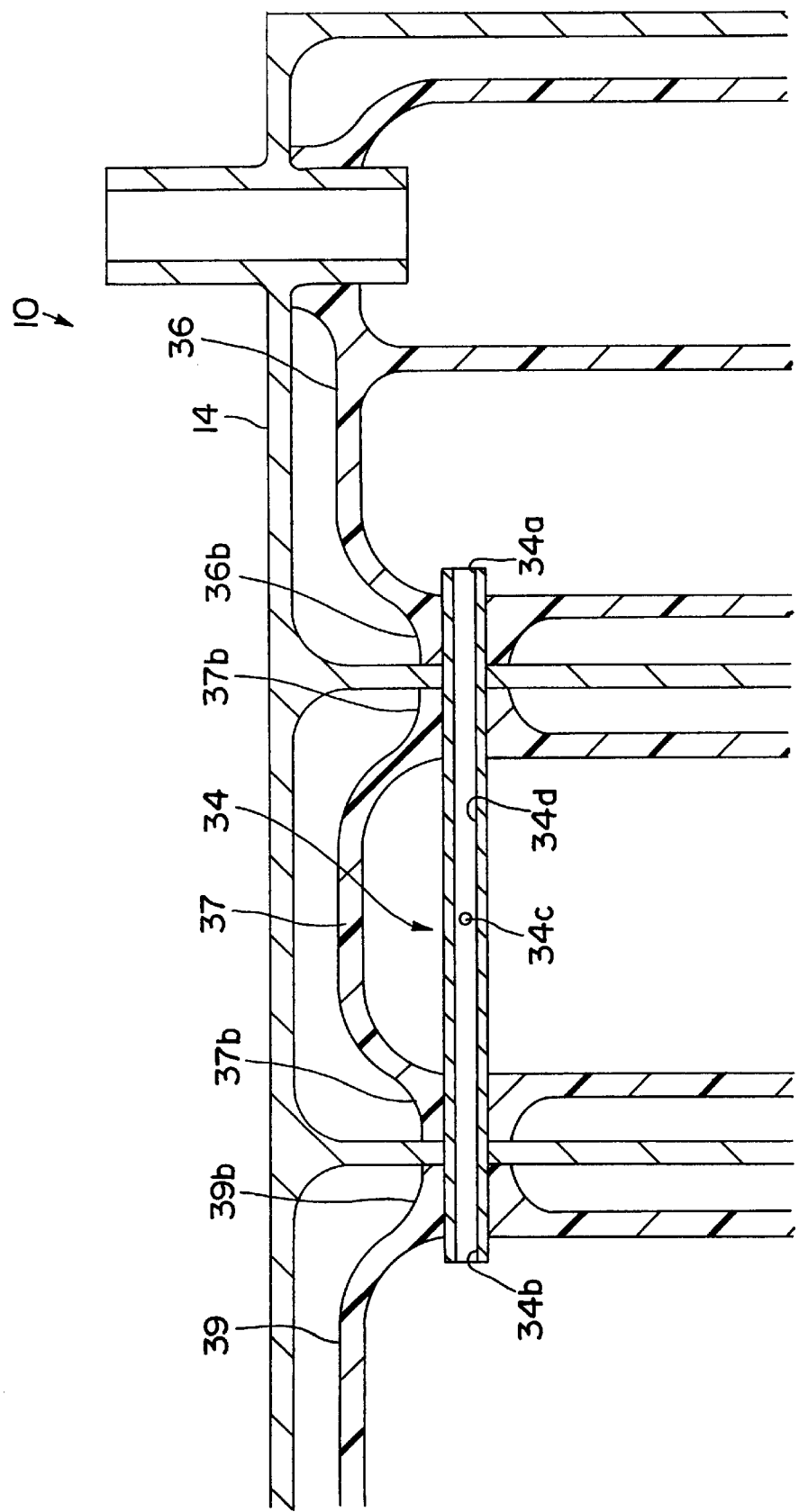
FIG. 1 is an enlarged fragmentary vertical section of the top portion of one embodiment of housing and bladder chambers according to the invention.
Figure 2:
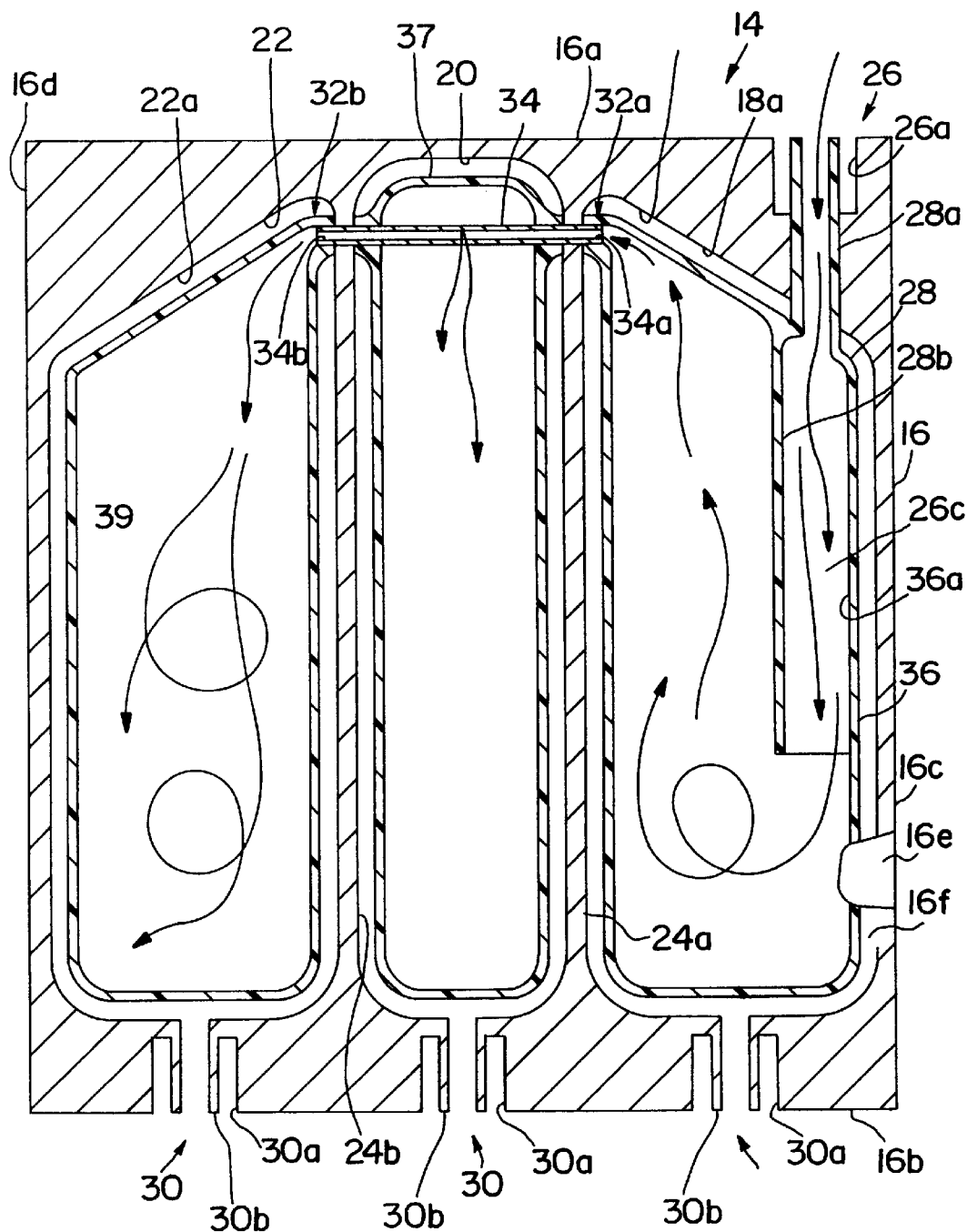
FIG. 2 is a full vertical section view of another embodiment of the housing and bladder chambers according to the invention.
Figure 3:
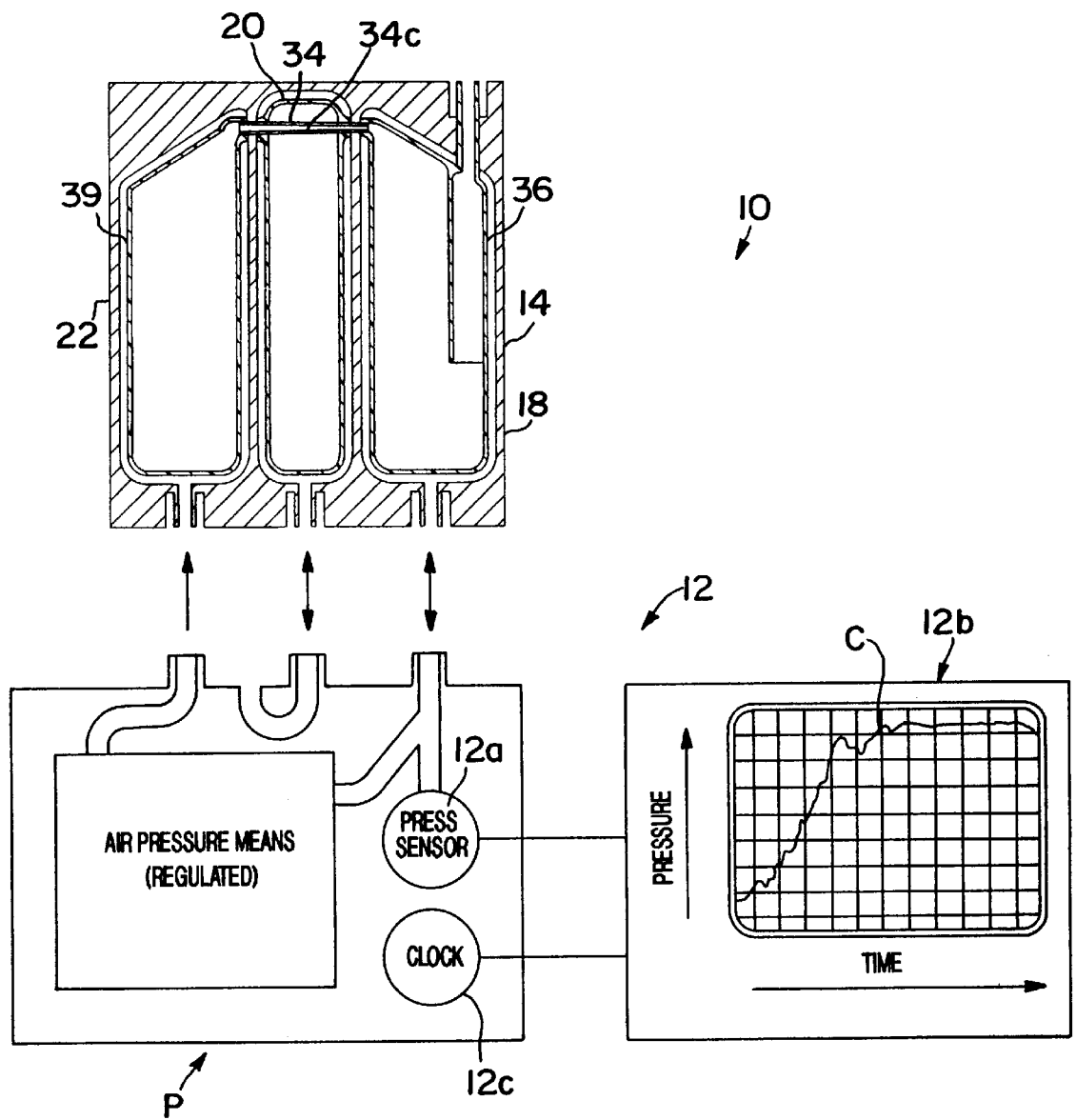
FIG. 3 is schematic view of the housing unit in position with respect to a test analyser according to the invention.

Referring to FIGS. 1–3 of the drawing, a blood coagulation test system 10 according to the invention comprises a test analyser 12 and a multiple chamber blood collection and test unit 14.

The test unit 14 (FIG. 2) comprises a rigid, upright, enclosed housing 16 fabricated of plastic or other suitable material and divided into a plurality of (preferably three) side-by-side air tight chambers 18, 20, 22 by upstanding interior partition walls 24 a–b. The housing is enclosed by top 16a, bottom 16b, side 16 c–d, front 16e, and rear 16f walls.

The housing includes an inlet opening 26 into the first chamber for receiving a blood sample through an inlet valve 28 fitted into the opening. The inlet opening may be recessed at 26a (as in FIG. 2) to accommodate a fitting (not shown) connecting the valve to a blood specimen supply tube.

Each housing chamber is provided with a pressure opening 30 located in the housing for applying fluid overpressure, underpressure, or ambient pressure to the interior of each chamber housing. The housing may be recessed at 30a about each pressure opening thereby defining a tube 30b for connection to external pressure fittings.

In preferred form as in FIGS. 2–6, the first and third chambers have inlet and outlet ports 32a–b at the highest point within each chamber for directing blood flow with minimal air entrainment into and away from the access 34a and exit 34b openings of a bleeding tube 34. Such highest point location may be achieved by the angled top chamber walls 18a, 22a shown in FIGS. 2–6, or by other means such as the high point of a domed chamber.

Each of the side-by-side housing chambers is completely lined with a flexible, air impervious film bladder 36, 37, 39 within the interior chamber. The bladder for the first chamber includes an integral one-way flow valve 28 including an inlet tube 28a fitted into the inlet opening, and a flexible skirt 28b cooperating with a section of bladder wall 36a to define a blood entry chamber 26c within the bladder chamber. The one-way flow valve allows flow of blood sample into the bladder chamber. Reverse flow cannot occur because the valve skirt will collapse against the section of bladder wall thereby effectively sealing the inlet tube when pressure is applied to a blood sample in the bladder chamber.

The bladders and inlet valve are fabricated of any plastic film suitable for handling clinical blood samples.

Initially, before any of the housing chambers is pressurized or evacuated and before any blood sample is taken, the bladders themselves are completely collapsed to void as much air as practicable. This is done to minimize the presence of air in the bladder chambers at all times when processing a blood specimen.

A bleeding tube 34 interconnects all three bladder chambers 36, 37, 39 preferably along the top portions of the chambers and extending through the upper reach of the partition walls 24a–b. The bleeding tube is supported by the partition walls, is fitted at opposite ends 34a, 34b to the first and third bladders, and passes through the intermediate bladder. The bladder walls are enlarged at their connections with the bleeding tube to form fluid tight seals 36b, 37b, 39b (FIGS. 1 & 5) that maintain fluid tight integrity of both housing chambers and bladder chambers over the entire pressure operating range of the test unit.

It is within the scope of the invention for the three film bladders to be sealed to each other at their inlet/outlet ports 36b, 37b, 37b' and 39b, and to be joined through these ports by a bleeding tube all without the need for supporting partitions and a supporting housing with housing chambers.

The bleeding tube 34 (FIGS. 2 & 5) has an access opening 34a for receiving a flow of blood at the top of the first bladder chamber. The tube has a bleeding hole or holes 34c intermediate its length for bleeding the blood sample into the second or intermediate bladder chamber. The bleeding hole or holes have a smaller diameter than the lumen 34d of the tube with a diametrical aspect ratio generally of 3:1 to 5:1. Actual hole diameter is from 0.005" to 0.010". Finally, the tube has an exit opening 34b for flow of the blood sample into the third or last of the chambers 39.

Figure 5:
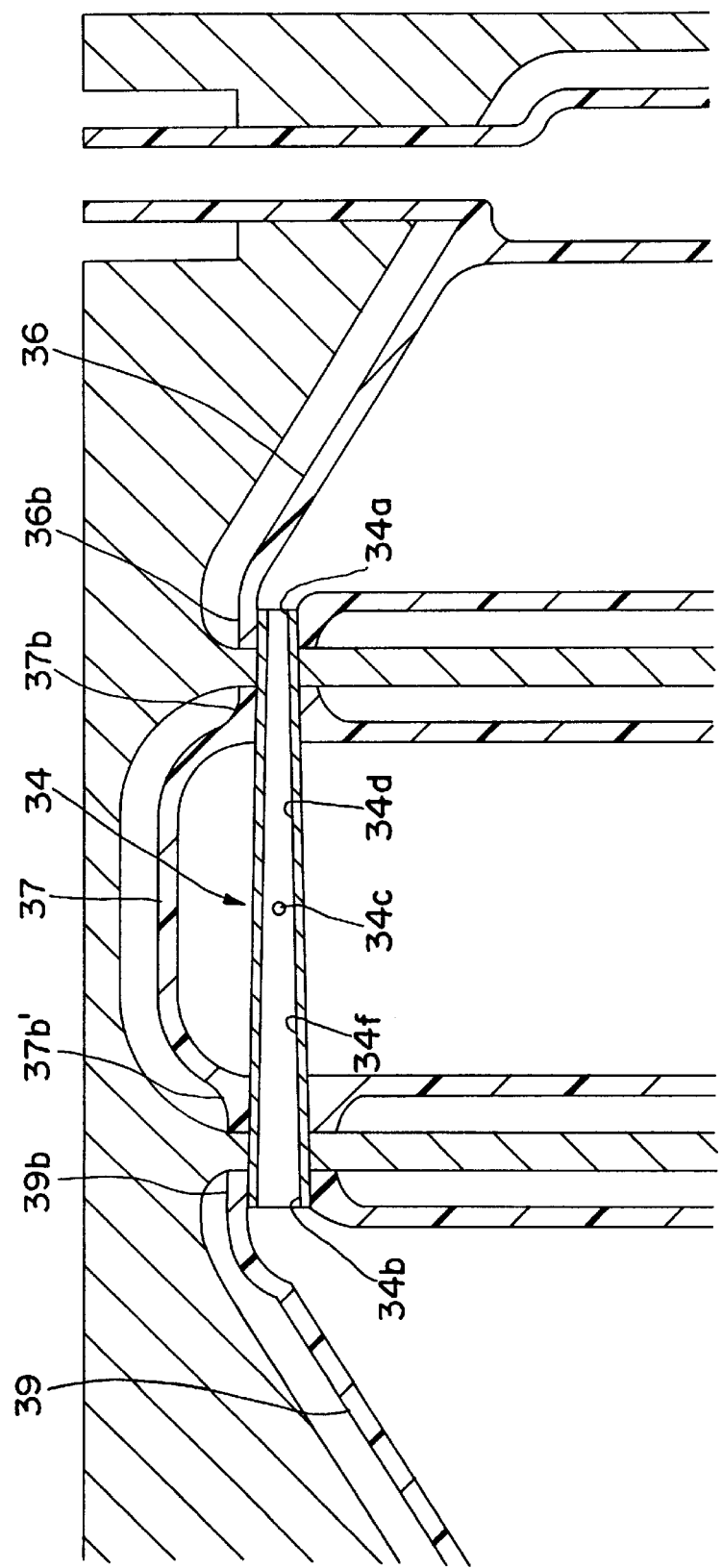
FIG. 5 is an enlarged fragmentary vertical section of the top portion of the embodiment of FIG. 4.

As shown in FIGS. 3–5, the bleeding tube may be tapered having an exit opening 34b diameter greater that its access opening 34a. The taper angle is preferably a manufacturing draft angle. The tapered configuration promotes immediate release of a clot from the tube surface at the point of thrombolysis, i.e., the point at which the clot shrinks or begins dissolving. At shrinkage, the clot releases from the tube wall and immediately passes along the tapered tube into the third bladder chamber. The system then reverts to normal flow of blood through the tube.

The material selected for the bleeding tube is preferably thrombogenic, for example, the tube may be fabricated entirely of any suitable thrombogenic material, or a tube base of plastic may have its inner surface 34f coated with a thrombogenic material such as collagen.

Air or fluid overpressure, underpressure, and ambient pressure are selectively applied to the housing chambers to manipulate the bladder chambers for the purpose of drawing blood into a bladder chamber, (i.e, underpressure), for expelling a blood sample from a chamber (i.e., overpressure), and for controlling blood flow into a chamber (i.e., overpressure) Preferably, the intermediate bladder chamber receives a bleeding sample with its housing chamber at ambient pressure.

In a modified embodiment of the invention shown in FIG. 4, the third chamber 22 does not have a pressure opening 30 of the first and second chambers. Instead, the third chamber is provided with a restricted fitting 40 defining an orifice 40a for exhausting air from the housing chamber at a controlled rate so as to maintain a system pressure of approximately 60 mm Hg on a blood sample entering bladder chamber 39 through the bleeding tube 34. The size of the orifice is selected using known principles.

The operation of the test unit is as follows.

First, in an infusion phase using a completely collapsed and voided first bladder 36, the first housing chamber 18 is evacuated through pressure opening 30 causing the bladder to expand and thereby draw a blood sample from a patient into the first bladder chamber through the one-way valve 28. The bladder is filled to a volume of approximately 2 ml of blood only. Blood entering the bladder is prevented from leaving by means of the one-way valve.

If desired, an intermediary device such as a syringe (not shown) may be interposed between patient and the test unit for taking a blood sample and transferring the sample to the bladder chamber 36.

As noted above, the third bladder is, initially, completely collapsed and voided of all air as is practicable.

Next, pressures are applied to the housing chambers to achieve two goals:
 (a) to initiate the test at a stabilized system pressure of 60 mm Hg (typical venous pressure), and
 (b) to restrain or control the blood flow rate through the system such that the 2 ml blood sample contained in the first bladder chamber 36 does not entirely pass into the destination bladder chamber 39 before normal hemostasis sets in, roughly 4–10 minutes.

So, a pressure source P (FIG. 3) with a potential in the range of 300 mm Hg is applied first to housing chamber 18, thereby compressing the first bladder 36 and driving its blood sample through the bleeding tube 34 into the destination bladder 39 in housing chamber 22. Typically, the destination bladder is quite flexible and allows relatively unimpeded blood to flow in rapidly at a very low pressure.

In order to control the system pressure to 60 mm Hg and to restrain the flow rate of the blood sample, an opposing pressure is established in the destination housing chamber 22, which is in turn transferred to the bladder 39 contained therein. Such opposing pressure is achieved either by (a) introducing a positive pressure to housing chamber 22, or (b) by restricting the outflow of air contained in said housing chamber with a pressure control orifice 40a shown in FIG. 4.

Additionally, a small pressure drop occurs across the bleeding hole 34c. The pressure drop is additively accounted for when calibrating the pressure differential required to stabilize the system pressure at approximately 60 mm Hg.

The typical test begins with blood flowing from bladder 36, through the bleeding tube 34, (with a small amount of blood exiting the bleeding hole 34c into bladder 20), and continuing on to into the destination bladder 39 at a stabilized system pressure of 60 mm Hg. As blood flows through the bleeding tube it starts to coagulate. As coagulation products continue to accumulate, the blood flow through the bleeding hole and the bleeding tube is progressively obstructed. The resulting occlusion creates a back pressure in the first chamber housing that exceeds the stabilized system pressure. The pressure increase over the elapsed time yields a profile of each patient's blood coagulation characteristics. Appropriate time sensor 12c and pressure sensors 12a translate data typically into a graph representation 12b, usually in the form of a chart C.

The intermediate housing chamber 20 may or may not receive pressure through its pressure port, with the normal condition being a passive state with exposure of the bladder exterior 37 to ambient pressure.

A modified form of the invention is illustrated in FIGS. 6a–c comprising a two chamber blood collection and test unit 50. The unit includes a two-chamber housing 52 of construction similar to that of FIGS. 2–5, however having a single interior partition 52a dividing the housing into similar air tight chambers 52b, 52c. The first housing chamber receives a first bladder 36 with inlet valve 28 all noted by the same reference numerals as FIGS. 2–5 for indicating identity of structure.

The second chamber 52c of FIG. 6a corresponds to the third chamber of FIGS. 2–5, so again, the same reference numerals are used indicating identity of structure.

The two bladder chambers are connected by a bleeding tube 54 in several variations. One tube 54a, FIG. 6b, includes a single bleeding passage 56 of approximately 0.005" to 0.010" diameter extending between the two chambers. Another tube 54b, FIG. 6c, has a plurality of holes 58a–d of different size ranging from 0.005" to 0.025" diameter between the two chambers.

The single bleeding passage 56, with chambers pressurized as for the first and third chambers described above, performs testing for blood clotting characteristics.

The multiple hole 58a–d bleeding tube (pressurized in the same way) allows specific events including hemostasis, thrombus, and thrombolysis to be recorded as each successive hole is occluded.

The two-chamber unit may be used without the housing. Instead, the bladders may be pressurized by externally applied force or weights.

The test cartridge and analyser provide in vitro blood analysis for hemostasis, and clot formation, reliably and repeatably immediately after sample collection under test conditions of constant temperature, pressure, and flow rate with minimal manipulation, agitation, and mechanical stress of the sample and with minimal disposal bulk. Once collected, the blood sample is confined to the test unit throughout testing and disposal thereby eliminating any opportunity for infecting personnel handling the unit in normal use. The system is particularly suited for use at patient sites and provides test results in a time period determined nearly entirely by the time required for collection of a sample and for occurrence of the blood functions being monitored.

Various changes may be made to the structure embodying the principles of the invention. The foregoing embodiments are set forth in an illustrative and not in a limiting sense. The scope of the invention is defined by the claims appended hereto.

I claim:

1. A blood coagulation test unit comprising a housing defining a plurality of housing chambers, openings in the housing for applying pressure into each of the housing chambers, each of the housing chambers having a film bladder defining a bladder chamber therein, means for admitting a blood sample into one of the bladder chambers, a tube for conducting blood flow between the bladder chambers, a bleeding hole in the tube for bleeding a portion of the sample into another bladder chamber, and pressure means for controlling the flow rate of blood through the tube in order to determine hemostasis, thrombus, and thrombolysis characteristics of the blood sample.

2. A blood coagulation test unit comprising a rigid housing having a plurality of housing chambers therein, an opening in the housing into each of said housing chambers for applying pressure into each of the chambers, each of the chambers having a film bladder defining a bladder chamber therein, means for admitting a blood sample into a first bladder chamber, a bleeding tube having a bleeding hole for bleeding a portion of the sample into another bladder chamber, and means for applying pressure to the bladder in a first housing chamber to establish blood flow through the bleeding tube, and means for controlling the flow rate of blood through the bleeding tube whereby hemostasis, thrombus and thrombolysis characteristics of the blood sample are determined.

3. A blood coagulation test unit as defined in claim 2 in which the means for admitting comprises an inlet opening through the housing into the first housing chamber, and a one-way flow valve cooperating with the inlet opening for flow of a blood sample into said first bladder chamber.

4. A blood coagulation test unit as defined in claim 3 in which the one-way flow valve includes a flexible skirt cooperating with a section of the bladder to allow blood flow into the bladder chamber, and to collapse against the bladder chamber to prevent back flow of blood through the valve.

5. A blood coagulation test unit comprising a rigid housing divided by interior partitions into three housing chambers, openings for applying pressure into each of the housing chambers, each of the housing chambers having an enclosed, air tight film bladder defining a bladder chamber therein, means for admitting a blood sample into a first bladder chamber, a bleeding tube passing through the partitions and interconnecting each of the bladder chambers, a bleeding hole in the bleeding tube for bleeding a portion of the sample into a second bladder chamber, the bleeding tube terminating at a third bladder chamber for receiving the remainder of the blood sample flowing through the bleeding tube, and means for establishing a pressure differential between the housing chambers having the first and the third bladder chambers therein to control the flow rate of blood through the bleeding tube in order to determine hemostasis, thrombus and thrombolysis characteristics of the blood sample.

6. A blood coagulation test unit as defined in claim 5 in which the second bladder chamber is at ambient pressure.

7. A blood coagulation test unit as defined in claim 5 in which the bleeding tube is tapered to facilitate release of blood clot from the tube wall at thrombolysis of the clot.

8. A blood coagulation test unit as defined in claim 5 in which the lumen:bleeding hole has a diametrical aspect ratio of between 3:1 to 5:1.

9. A blood coagulation test unit comprising a rigid housing divided by interior partitions into three housing chambers, openings for applying pressure into two of the housing chambers, an orifice for controlling back pressure in the third housing chamber, each of the housing chambers having an enclosed, air tight film bladder defining a bladder chamber therein, means for admitting a blood sample into a first bladder chamber, a bleeding tube passing through the partitions and interconnecting each of the bladder chambers, a bleeding hole in the bleeding tube for bleeding a portion of the sample into a second bladder chamber, the bleeding tube terminating at a third bladder chamber for receiving the remainder of sample flowing through the bleeding tube, and means for establishing a pressure differential between the housing chamber having the first and the third bladder chambers therein to control the flow rate of blood through the bleeding tube in order to determine hemostasis, thrombus and thrombolysis characteristics of the blood sample.

10. A blood coagulation test unit comprising a rigid housing divided by an interior partition into two housing chambers, openings for applying pressure into each of the housing chambers, each of the housing chambers having an enclosed, air tight film bladder defining a bladder chamber therein, means for admitting a blood sample into one of the bladder chambers, a bleeding tube passing through the partition and interconnecting the bladder chambers defining a passage for flow of the blood sample between the bladder chambers, and means for establishing a pressure differential between the first and second housing chambers to control the flow rate of blood through the bleeding tube in order to determine hemostasis, thrombus, and thrombolysis characteristics of the blood sample.

11. A blood coagulation test unit as defined in claim 10 in which the bleeding tube has a single passage therein.

12. A blood coagulation test unit as defined in claim 11 in which the single passage diameter is approximately 0.005" to 0.010".

13. A blood coagulation test unit as defined in claim 10 in which the bleeding tube has a plurality of passages therein.

14. A blood coagulation test unit as defined in claim 13 in which the passage diameters are in a range of approximately 0.005" to 0.025".

15. A blood coagulation test unit comprising a plurality of enclosed, air tight film bladders defining bladder chambers, means for admitting a blood sample into one of the bladder chambers, a bleeding tube interconnecting each of the bladder chambers for defining a blood flow path between the bladder chambers, a bleeding hole in the bleeding tube for bleeding a portion of the sample into another bladder chamber, and means for establishing a pressure differential between the bladder chambers to control the flow rate of blood through the bleeding tube in order to determine chacteristics of the blood sample.

16. A blood coagulation test unit comprising a rigid housing having a plurality of housing chambers therein, an opening in the housing into each of said housing chambers for applying pressure into each of the chambers, each of the chambers having a film bladder defining a bladder chamber therein, the bladder chambers being collapsed and as air free as practicable, means for admitting a blood sample into one bladder chamber, means for evacuating one housing chamber containing said one bladder chamber to aid in drawing a blood sample into the one bladder chamber, a bleeding tube interconnecting the bladder chambers, a bleeding hole in the bleeding tube for bleeding a portion of the sample into another bladder chamber, and means for applying pressure to the one bladder in said one housing chamber to establish blood flow through the bleeding tube, and means for controlling the flow rate of blood through the bleeding tube whereby hemostasis, thrombus, and thrombolysis characteristics of the blood sample are determined.

17. The combination of blood coagulation test unit and a test analyser comprising a housing defining a plurality of housing chambers, openings in the housing for applying pressure into each of the housing chambers, each of the housing chambers having a film bladder defining a bladder chamber therein, means for admitting a blood sample into one of the bladder chambers, a tube for conducting blood flow between the bladder chambers, a bleeding hole in the tube for bleeding a portion of the sample into another bladder chamber, and pressure means for controlling the flow rate of blood through the tube; the test anaylser being connected to the housing chambers to monitor pressure changes therein and to provide a pressure/time correlation for blood characteristics including hemostasis, thrombus, and thrombolysis.

* * * * *